United States Patent [19]

Sabourin et al.

[11] 4,210,610

[45] Jul. 1, 1980

[54] PROCESS FOR THE PREPARATION OF CHLOROARYLACETYLENE PRECURSORS

[75] Inventors: Edward T. Sabourin, Allison Park; Charles M. Selwitz, Monroeville, both of Pa.

[73] Assignee: Gulf Research and Development Company, Pittsburgh, Pa.

[21] Appl. No.: 967,247

[22] Filed: Dec. 7, 1978

[51] Int. Cl.$^2$ .................. C07C 17/00; C07C 29/00
[52] U.S. Cl. .................. 260/649 R; 260/649 DP; 260/650 R; 568/807; 568/812; 568/813
[58] Field of Search .............. 568/713, 807, 808, 809, 568/811, 812, 813; 260/646, 649 R, 650 R, 649 DP

[56] References Cited

U.S. PATENT DOCUMENTS

| 2,693,489 | 11/1954 | Kleurschmidt | 568/813 |
| 3,981,932 | 9/1976 | Diamond | 260/645 |
| 4,089,908 | 5/1978 | Kathawala | 568/813 |

OTHER PUBLICATIONS

Moroz et al., "C.A." 78:147456x (1973).
Sonogashua et al., "Tetra. Letters", No. 50, pp. 4467–4470 (1975) Pergamon Press.
Curtis et al., "Tetra Letters", No. 25, pp. 2919–2920 (1968) Pergamon Press.

*Primary Examiner*—Norman Morgenstern

[57] ABSTRACT

Chloroarylacetylenes such as m-chlorophenylacetylene and certain precursors to such chloroarylacetylene are prepared by reacting a chloroarylbromide with a substituted terminal acetylene compound containing at least three carbon atoms and a hydroxy group on the carbon atom adjacent to the acetylene group in the presence of a dialkyl or trialkyl amine solvent and a catalyst system consisting of a palladium complex containing two halogen moieties and two tri-substituted phosphine moieties. Additional triphenylphosphine can be added. A cuprous iodide promoter is also employed in the reaction sequence.

17 Claims, No Drawings

PROCESS FOR THE PREPARATION OF CHLOROARYLACETYLENE PRECURSORS

This invention relates to a process for producing chloroarylhydroxy substituted acetylenes and in particular for producing 2-methyl-4-(3-chlorophenyl)-3-butyn-2-ol and their subsequent conversion to a chloroarylacetylene.

BACKGROUND OF THE INVENTION

U.S. Pat. No. 3,981,932 issued on Sept. 21, 1976 to Julius Diamond and entitled "Ethynylbenzene Compounds and Derivatives Thereof" relates to certain novel ethynylbenzene compounds having pharmacological properties which are useful for the relief and inhibition of inflammation conditions including arthritic conditions without undesired side effects such as gastric hemorrhage or ulceration. In addition Diamond teaches his compounds possess analgesic and antipyretic properties useful in the treatment of pain and fever.

Among the compounds found useful by Diamond are chloroarylacetylenes. Diamond's preparatory techniques are described in Columns 4 through 7 and are quite complex.

DESCRIPTION OF THE PRIOR ART

An article entitled, "A Convenient Synthesis of Acetylenes: Catalytic Substitution of Acetylenic Hydrogen with Bromoalkenes, Iodoarenes, and Bromopyridines" by Kenkichi Sonogashira et al., published in Tetrahedron Letters, No. 50, pages 4467–4470, 1975 (Pergamon Press, Gr. Brit.), suggests that iodobenzene could be reacted with acetylene in the presence of a complex catalyst system to produce phenylacetylene. There is no suggestion in the article that bromobenzene or other bromopyridines could be substituted for the iodoarene compounds. An attempt was made to react meta-nitrobromobenzene with acetylene using the same catalyst under the same conditions and using the same solvent as taught by Sonogashira et al., but no reaction was observed after six hours, the six hours being the same time period as used by Sonogashira et al. for the reaction of acetylene with iodobenzene. Sonogashira et al. also present working examples using other acetylenic reactants besides acetylene, namely certain substituted terminal acetylenes, including 2-propyn-1-ol (HC≡C—CH₂—OH) and phenylacetylene. An attempt was then made to react bromobenzene with an analog of 2-propyn-1-ol, i.e. 2-methyl-3-butyn-2-ol using the same conditions as taught by Sonogashira et al., except the temperature was increased from room temperature to 56° C., and it was found, as will be shown more fully below, that the reaction was extremely sluggish, despite the higher temperature, so that the result was of substantially no interest from a commercial standpoint.

Earlier work has been done in Russia relating to acetylenic condensation and is contained in an article by M. S. Shvartsberg et al. in Izvestiya Akademii Nauk SSSR, Seriya Khimicheskaya, No. 2, pages 476–479 (1973). The Russian work indicates that chloroiodobenzene can be reacted with rather complex substituted acetylenes in the presence of a potassium carbonate—copper catalyst system to produce chlorophenyl substituted acetylenes, which can be hydrolyzed to form less complex substituted chlorophenylacetylenes, which can be further reacted with a weak base to form chlorophenylacetylene. There is no indication or teaching in the Russian article that the bromo analog of the iodochlorobenzene can be employed using the peculiar base catalyst of the Russians. It would thus appear from the prior art that iodobenzene (Sonogashira et al.) or chloroiodobenzene (Shvartsberg et al.) will work in different catalyst systems with various types of acetylenic or substituted acetylenic charge stocks in such a manner that the acetylenic charge stock substitutes for the iodo group on the benzene nucleus. None of the prior art, however, dictates that bromoarenes can be employed in either of the catalyst systems of the prior art.

Surprisingly, however, and in accordance with the invention, it has been found that chloroarylhydroxy substituted acetylenes can be prepared from a chloroarylbromide by the reaction of the cloroarylbromide with a substituted terminal acetylene compound containing at least 3 carbon atoms and a hydroxy group on the carbon atom adjacent to the acetylene group at mild conditions to produce a substantial yield of a chloroarylhydroxy substituted acetylene. The reaction occurs in the presence of an amine-type solvent, which serves not only as a solvent but also as a complexing agent with the by-product HBr, which is produced during the reaction. The substitution reaction is catalyzed by a complex palladium salt containing two halogen moieties and two substituted phosphine moieties where the substituents on the phosphorus are phenyl, lower alkyl groups and substituted phenyl groups. The catalytic activity of the palladium complex salt is promoted with a small amount of cuprous iodide.

Any chloroarylbromide can suitably be employed in the process of this invention. The source of the chloroarylbromide is not critical and its method of preparation forms no part of this invention.

Preferred are chloroarylbromides having the formula:

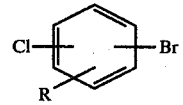

where R can be H, alkyl having from 1 to 10 carbon atoms, preferably 1 to 4 carbon atoms, phenyl, and cycloalkyl having from 5 to 6 carbon atoms.

Suitable non-limiting examples of chloroarylbromides useful in the process of this invention are:

m-, o- and p-chlorobromobenzene
2-chloro-4-bromotoluene
2-chloro-6-bromotoluene
2-chloro-4-bromoethylbenzene
2-chloro-6-bromoethylbenzene
2-chloro-4-bromocyclohexylbenzene
2-chloro-6-bromocyclohexylbenzene
2-chloro-4-bromobiphenyl
2-chloro-6-bromobiphenyl
2-chloro-3-bromonaphthalene
1-chloro-8-bromonaphthalene
2-chloro-4-bromopropylbenzene
2-chloro-6-bromohexylbenzene
2-chloro-6-bromononylbenzene
2-chloro-4-bromoisobutylbenzene The chloroarylbromide is reacted with a substituted terminal acetylene compound containing at least 3 carbon atoms and a hydroxy group on the carbon atom adjacent to the acetylene group. The preferred substituted terminal acetylene compounds are those having the formula:

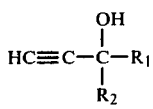

where $R_1$ and $R_2$ can be the same or different and are selected from the group consisting of hydrogen, lower alkyl groups having from 1 to 4 carbon atoms, phenyl, substituted phenyl; or where $R_1$ and $R_2$ can form a saturated 5- or 6-membered ring. The preparation of these compounds is well known in the art and forms no part of the subject invention. For example, acetylene can be reacted with acetone to form 2-methyl-3-butyn-2-ol, which is the preferred substituted terminated acetylenic charge stock for use in the process of this invention. Other suitable acetylenic compounds include the following:

3-methyl-1-pentyn-3-ol;
3-ethyl-1-pentyn-3-ol;
2-phenyl-3-butyn-2-ol;
1-ethynylcyclohexanol; and
1-ethynolcyclopentanol.

Usually the chloroarylbromide is reacted with the terminal acetylene compounds in a molar ratio of about 1:1, but suitable molar ratios include those from 0.4:1 to 1.5:1 and are more preferably from 0.95:1 to 1:1.05.

The reaction of the chloroarylbromide with the terminal acetylenic compounds defined above occurs in the presence of a dialkyl or trialkyl amine solvent and a complex catalyst system. The amine solvent can suitably have the formula:

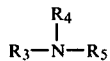

where $R_3$, $R_4$ and $R_5$ can be the same or different and are selected from the group consisting of hydrogen and lower alkyl groups having from 1 to 4 carbon atoms, with the proviso that no more than one of said R groups can be hydrogen. Suitable solvents include but are not limited to dimethylamine, trimethylamine, diethylamine, triethylamine, ethylpropylamine, ethylbutylamine and dibutylamine.

The catalyst employed is a complex palladium salt containing two halogen moieties, where the halogen is selected from the group consisting of bromine, iodine and chlorine, and two trisubstituted phosphine moieties where the constituents are selected from phenyl, alkyl groups having from 1 to 4 carbon atoms, and substituted phenyl groups. A suitable palladium complex would have the formula:

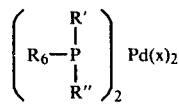

where x is bromine, iodine or chlorine, and $R_6$, $R'$ and $R''$ are the same or different and are selected from the group consisting of phenyl groups. The substituents on the phenyl groups can include alkyl groups having from 1 to 4 carbon atoms, alkoxy groups having 1 to 4 carbon atoms, and halogen. A suitable list of representative palladium complex salts which can be employed in the process of this invention include:

bis(triphenylphosphine)palladium dibromide;
bis(tri-n-butylphosphine)palladium dichloride;
bis(tri-t-butyl-phosphine)palladium dichloride;
bis(tri-i-butylphosphine)palladium dichloride;
bis(triethylphosphine)palladium dichloride;
bis(tripropylphosphine)palladium dichloride;
bis(tritolylphosphine)palladium dichloride;
bis(trianisylphosphine)palladium dichloride;
bis(tri(chlorophenyl)phosphine)palladium dichloride; and
bis(tri(bromophenyl)phosphine)palladium dichloride.

The palladium catalyst can be added to the reaction mixture as such or can be formed in situ in the reaction mixture by the separate addition of a palladium salt having the formula $Pd(x)_2$ where x is as defined, and a trisubstituted phosphine compound having the formula:

where $R_6$, $R'$ and $R''$ are as defined and wherein the molar ratio of the trisubstituted phosphine to the palladium is about 2:1. If desired, the reaction can occur in the presence of excess trisubstituted phosphine, e.g. triphenylphosphine, over and above that necessary to form the palladium catalyst.

Whether the palladium catalyst is formed in situ or whether the palladium catalyst is formed separately and added to the reaction system, the molar ratio of the trisubstituted phosphine compound to palladium in the reaction system is above 2:1, and can suitably be from 2.5:1 to 50:1.

A promoter for the catalyst system is also employed, and this promotor comprises cuprous iodide. Usually the amount of the promoter is very small, and suitable amounts of promoter include a molar ratio of promoter to palladium catalyst of from 0.5:1 to 20:1, preferably from 1:1 to 5:1. The amount of the palladium catalyst employed in the reaction is usually from 0.01 to 1.0 mole percent based on the chloroarylbromide and is more preferably from 0.02 to 0.05 mole percent based on the chloroarylbromide.

The reaction of the chloroarylbromide with the acetylene-terminated compound is really a substitution-type reaction, and the reaction conditions to employ are relatively mild and include a temperature from about 20° to 200° C. and more preferably from 50° to 125° C. However, it is considered that the reaction conditions are not critical, and the precise reaction conditions to employ would be obvious to one having ordinary skill in the art. The reaction conditions should be such that the solvent chosen is maintained in the liquid phase. The normal reaction pressure is atmospheric; however, increased reaction pressures of up to 250 psig (1.7 MPa) or higher can be employed. The reaction time to employ is somewhat dependent on the particular charge stock and catalyst chosen and, of course, on the reaction temperature. Usually the reaction time is from 1 hour to 150 hours, but is more usually from 3 hours to 24 hours. Higher or lower reaction times can be employed, for timing is not a critical parameter but rather in many cases serves to increase the yield of the desired reaction product.

A typical reaction sequence is shown in Equation 1 below, which utilizes certain specific charge stocks which fall within the scope of the charge stocks defined above.

Equation 1

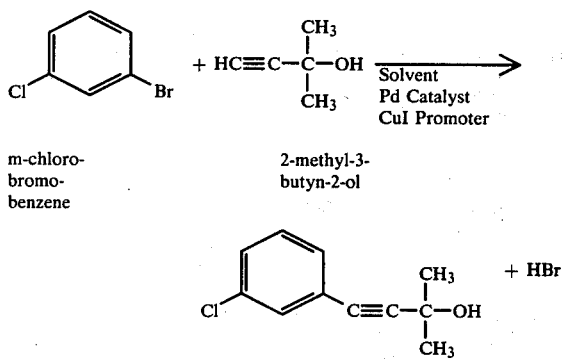

m-chloro-bromo-benzene  2-methyl-3-butyn-2-ol

Referring to Equation 1 above, it can be seen that a by-product of the reaction sequence is HBr. The HBr cannot be permitted to remain in the reaction product because of its corrosive nature.

It is one of the purposes of the amine solvent to react with the HBr in order to produce the amine hydrobromide salt and render it inactive. The amount of the amine solvent to employ in the reaction is not critical but must thus be sufficient to maintain the reactants in the liquid phase plus provide sufficient amine to react with the by-product HBr. Amounts of solvent from 500 to 700 ml per mole of chlorobromobenzene have successfully been employed. However, greater or lesser amounts can be employed, and the particular amount to employ would be within the normal skill in the art given the criteria set forth above.

The invention will be further described with reference to the following experimental work.

In all of the experiments to follow, a 3-necked flask equipped with a magnetic stirrer, thermometer, condenser, nitrogen inlet and outlet, a rubber septum sample port and a heating mantle was employed. The flask was charged with the chlorobromobenzene, the acetylenic charge stock, the catalyst and the amine solvent. The sytem was then purged with nitrogen for 20 minutes, after which the cuprous iodide was added and the system brought to reaction temperature. Small samples of the reaction mixture were periodically withdrawn by syringe and were subjected to analysis by gas chromatography; and in this manner the reaction was monitored.

Upon termination, the reaction mixture was cooled to room temperature. The reaction solvent was then stripped from the reaction product on a rotary evaporator, followed by the addition of water to the residue to dissolve the salts and any residual amine solvent. Extraction of the aqueous mixture with toluene served to separate the product from the water-soluble components. The organic extract in toluene was then passed through a short column of 200-mesh alumina to remove the palladium catalyst and the cuprous iodide promoter. The toluene was then stripped to provide a crude product. In some cases the product was analyzed at this point by gas liquid chromatography with the aid of mesitylene as an internal standard. In other cases the product was distilled and the distilled product subjected to elemental analysis.

EXAMPLE 1

In the run for this example, m-chlorobromobenzene was reacted under a nitrogen atmosphere with 2-methyl-3-butyn-2-ol

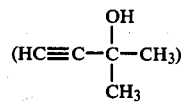

using [(C$_6$H$_5$)$_3$P]$_2$PdCl$_2$ as the catalyst; CuI as the promoter and triethylamine as the solvent. The conversion was 98.4 and the yield of

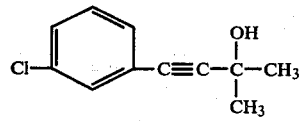

was 87.7%. The results are summarized in Table 1 below.

EXAMPLE 2

Example 1 was substantially repeated except the charge stock was p-chlorobromobenzene, and similar results were observed, as summarized in Table 1 below. The product, of course, was

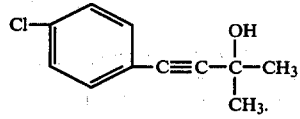

EXAMPLE 3

Example 2 was repeated except the reaction temperature was reduced to 56° C., the reaction time was increased and the solvent was diethylamine. The conversion was high (99%), but the selectivity was poor (61%), resulting in a reduced yield of

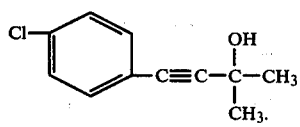

EXAMPLE 4

Example 1 was repeated except the charge stock was m-dichlorobenzene and no conversion was observed. The results are summarized in Table 1 below.

TABLE 1

Conversion of Chlorobromobenzene to 2-methyl-4-(m- or p-chlorophenyl)-3-butyn-2-ol

| Ex. No. | Substrate | Methyl-butynol mmoles | [(C6H5)3P]2 PdCl2 mmoles | CuI mmoles | Solvent (amine) (ml) | Reaction Time Hrs | Reaction Temp. °C. | % Conversion | % Selec. | % Yield[a] |
|---|---|---|---|---|---|---|---|---|---|---|
| 1 | m-Cl-C6H4-Br | 500 | 600 | 0.28 | 0.05 | Triethyl (300) | 90 | 90–100 | 98.4 | 89.1 | 87.7 |
| 2 | p-Cl-C6H4-Br | 10 | 10 | 0.07 | 0.05 | Diethyl (600) | 118 | 56 | 99.0 | — | — |
| 3 | " | 1000 | 1190 | 0.42 | 0.05 | Triethyl (600) | 90 | 90–100 | 99.0 | 93.6 | 92.7 |
| 4 | Cl-C6H4-Cl | 200 | 202 | 0.07 | 0.05 | Triethyl (200) | 21 | 90–100 | 0 | — | — |
| 5 | Br-C6H4-NO2 | 10 | [b] | 0.07 | 0.05 | Diethyl (60) | 6 | ambient | 0 | 0 | 0 |
| 6 | C6H5-Br | 10 | 10 | 0.07 | 0.25 | Diethyl (60) | 116 | 56 | 13 | — | — |

[a]Product in Exs. 1–3 is Cl-C6H4-C≡C-C(OH)(CH3)2; no trace of (CH3)2(OH)C-C≡C-C6H4-C≡C-C(OH)(CH3)2 found.

[b]Acetylene bubbled through solution continuously.

Referring to Table 1 above, the Conversion was a weight percent conversion and was calculated by:

$$\frac{\text{Initial wt chlorobromobenzene} - \text{Final wt chlorobromobenzene}}{\text{Initial wt chlorobromobenzene}} \times 100$$

Selectivity ("Selec.") in Table 1 means:

$$\frac{\text{Moles 2-methyl-4-(3- or 4-chlorophenyl)-3-butyn-2-ol}}{\text{Initial moles chlorobromobenzene} - \text{Final moles chlorobromobenzene}} \times 100$$

The Yield means the yield of 2-methyl-4-(3- or 4-chlorophenyl)-3butyn-2-ol:

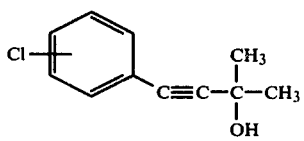

and was calculated as the product of Conversion times Selectivity. Selectivities and yields were calculated only on isolated crude products by gas chromatography with an appropriate internal standard (mesitylene).

EXAMPLE 5

Example 1 was repeated except nitrobromobenzene was used in lieu of the chlorobromobenzene, and after six hours no reaction was noted by continuous gas liquid chromatographic analysis. The results are summarized in Table 1 above.

Example 5 illustrates acetylene does not react with nitrobromobenzene. This perhaps is not surprising since the teachings of Sonogashira et al are specific to the reaction of acetylene with iodoarenes or bromoalkenes.

EXAMPLE 6

Example 1 was repeated except bromobenzene was the halide employed; the amount of CuI was increased to 0.25 mmol, and the reaction temperature was increased to 56° C. After 116 hours, the conversion was merely 13%. Selectivities and yields were not determined. The results are summarized in Table 1 above.

Referring to Table 1, a comparison of Examples 1–3 with Example 6 shows the presence of the chloro group on the charge stock activates the bromo group so that excellent conversions and yields of the desired product are obtained. Example 4, on the other hand, shows a dichlorobenzene to be inactive.

The chloroarylhydroxy substituted acetylenes produced as described above can be cleaved to produce the corresponding chloroarylacetylene by contacting the chloroaryl hydroxy substituted acetylene with an alkali metal hydroxide such as sodium hydroxide under mild conditions. Preferably, although not necessarily, the contacting occurs in the presence of an organic solvent, usually aromatic, at the reflux temperature of the solvent, and, of course, with good and adequate mixing.

For example, the 2-methyl-4-(3-chlorophenyl)-3-butyn-2-ol can be converted to m-chlorophenylacetylene by contact of the former compound with NaOH in toluene as shown in Example 12 below.

EXAMPLE 7

A portion of 2-methyl-4-(3-chlorophenyl)-3-butyn-2-ol is dissolved in toluene containing a minor amount of powdered NaOH. The mixture is refluxed for several hours to effect substantially complete conversion of the charge stock to chlorophenylacetylene.

Resort may be had to such variations and modifications as fall within the spirit of the invention and the scope of the appended claims.

We claim:

1. A process for the production of a chloroaryl hydroxy substituted acetylene which comprises:
    reacting a chloroarylbromide with a substituted terminal acetylene compound containing at least three carbon atoms and an hydroxy group on the carbon atom adjacent to the acetylene group in the presence of a solvent comprising a compound having the formula:

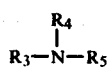

where $R_3$, $R_4$, and $R_5$ can be the same or different and are selected from the group consisting of hydrogen and lower alkyl groups having from 1 to 4 carbon atoms with the proviso that no more than one of said R groups can be hydrogen, and in the added presence of:
    a catalyst comprising a compound having the formula:

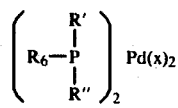

where x can be Br, I, or Cl;
    and where $R_6$, $R'$ and $R''$ can be the same or different and are selected from the group consisting of phenyl, substituted phenyl and alkyl groups having from 1 to 4 carbon atoms;
    and a promotor comprising cuprous iodide; to produce HBr and the resultant chlorophenyl hydroxy substituted acetylenes.

2. A process according to claim 1 wherein the chloroarylbromide has the formula:

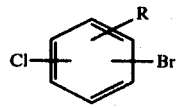

where R can be H, alkyl having from 1 to 10 carbon atoms, phenyl, and cycloalkyl having from 5 to 6 carbon atoms.

3. A process according to claim 2 wherein R in said chloroarylbromide is hydrogen.

4. A process in accordance with claim 1 wherein the terminal acetylene compound has the formula:

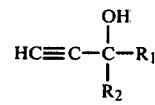

where $R_1$ and $R_2$ can be the same or different and are selected from the group consisting of hydrogen and lower alkyl groups having from 1 to 4 carbon atoms, phenyl and substituted phenyl, and where $R_1$ and $R_2$ can form a saturated 5- or 6-membered ring.

5. A process in accordance with claim 4 wherein $R_1$ and $R_2$ in the terminal acetylene compound are both methyl and wherein the resultant chlorophenylacetylene is 2-methyl-4-(chlorophenyl)-3-butyn-2-ol.

6. A process in accordance with claim 5 wherein the chlorobromobenzene is meta-chlorobromobenzene and the resultant chlorophenylacetylene is 2-methyl-4-(3-chlorophenyl)-3-butyn-2-ol.

7. A process in accordance with claim 6 wherein the molar ratio of the chlorobromobenzene to said substituted terminal compound is about 1:1.

8. A process in accordance with claim 7 wherein the catalyst is bis(triphenylphosphine)palladium dichloride.

9. A process in accordance with claim 8 wherein the solvent is triethylamine.

10. A process in accordance with claim 9 wherein the solvent is diethylamine.

11. A process in accordance with claim 1 wherein the resultant chloroarylhydroxy substituted acetylene compound is converted to a chloroarylacetylene by reacting said chloroarylhydroxy substituted acetylene compound with an alkali metal hydroxide in the presence of a solvent for said acetylene compound.

12. A process in accordance with claim 11 wherein the alkali metal hydroxide is sodium hydroxide.

13. A process in accordance with claim 12 wherein the solvent is toluene.

14. A process in accordance with claim 13 wherein said reaction is operated at reflux conditions.

15. A process in accordance with claim 1 wherein excess trisubstituted phosphine over that amount required to form said catalyst is present in the process.

16. A process according to claim 3 wherein the chloroarylbromide is meta-chlorobromobenzene.

17. A process according to claim 3 wherein the chloroarylbromide is para-chloro-bromobenzene.

* * * * *